(12) United States Patent
Remon (10) Patent No.: US 6,923,984 B1
(45) Date of Patent: Aug. 2, 2005

(54) CUSHIONING WAX BEADS FOR MAKING SOLID SHAPED ARTICLES

(75) Inventor: Jean Paul Remon, Melle (BE)

(73) Assignee: Universiteit Gent, Gent (BE)

( * ) Notice: Subject to any disclaimer, the term of this patent is extended or adjusted under 35 U.S.C. 154(b) by 183 days.

(21) Appl. No.: 09/831,422

(22) PCT Filed: Jul. 26, 2000

(86) PCT No.: PCT/EP00/07175

§ 371 (c)(1),
(2), (4) Date: Jul. 24, 2001

(87) PCT Pub. No.: WO01/21155

PCT Pub. Date: Mar. 29, 2001

(30) Foreign Application Priority Data

Sep. 17, 1999 (GB) .......................................... 9921933

(51) Int. Cl.⁷ ................................................. A61K 9/20
(52) U.S. Cl. ........................ 424/464; 424/489; 424/490
(58) Field of Search ................................. 424/464, 489, 424/490, 400

(56) References Cited

U.S. PATENT DOCUMENTS

| | | | | |
|---|---|---|---|---|
| 4,590,062 A | * | 5/1986 | Jang ............................. | 424/469 |
| 5,656,296 A | * | 8/1997 | Khan et al. .................. | 424/473 |

FOREIGN PATENT DOCUMENTS

| | | |
|---|---|---|
| GB | 1598458 | 9/1981 |
| WO | WO 89/02742 | 4/1989 |
| WO | WO 98/25590 | 6/1991 |
| WO | WO 97/25029 | 7/1997 |
| WO | WO 98/09597 | 3/1998 |

OTHER PUBLICATIONS

S.R. Bechard and J.C. Leroux, Drug Development and Industrial Pharmacy (1992) 18: 1927–1944, entitled "coated pelletized dosage form: effect compaction on drug release".
T.E. Beckert et al., International Journal of Pharmaceutics (1996) 143: 13–23, entitled "compression of enteric coated pellets to disintegrating tablets".
M. Celik and L. Maganti, Drug Development and Industrial Pharmacy (1994) 20: 3151–3173, entitled "formulation and compaction of microspheres".
R. Bodmeier, European Journal of Pharmaceutics and Biopharmaceutics (1997) 43: 1–8, entitled "tableting of coated pellets".
S.A. Altaf et al., Drug Development and Industrial Pharmacy (1999) 25: 635–642, entitled "Bead compacts: evaluation of rapidly disintegrating nonsegregating compressed bead formulations".
M. El-Mahdi et al., J. Macroencapsulation (2000) 17: 133–144, entitled "tableting of coated ketoprofen pellets".
L.A. Felton et al., S.T.P. Pharma sciences (1997) 6: 457–462, entitled "compaction properties of individual nonpareil beads coated with an acrylic resin copolymer".
G.F. Palmieri et al., S.T. P. Pharma sciences (1996) 6: 118–121, "drug release from compressed Eudragit RS30D coated beads".
J.J. Torrado and L.L. Augsburger, International Journal of Pharmaceutics (1994) 106: 149–155, entitled "effect of different excipients on the tableting of coated particles".
K.G. Wagner et al., S.T. P. Pharma sciences (2000) 10: 327–334, entitled "pellet–containing tablets: examination of distribution and deformation behaviour".
Burger, "Hunnius Pharmazeutisches Worterbuch", Walter de Gruyter, Berlin 7th ed., 1993, p. 1498.
Ohropax Wachskugelen found at www.ohropax.de/wachs-.htm.
Kydonieus, "Treatise on Controlled Drug Delivery", Marcel Dekker, Inc, NY, 1992, pp. 255, 284–295.

\* cited by examiner

*Primary Examiner*—Thurman K. Page
*Assistant Examiner*—Sharon Howard
(74) *Attorney, Agent, or Firm*—Barnes & Thornburg (57) ABSTRACT

Biologically inactive cushioning beads comprise at least one compressible cushioning component consisting essentially of a microcrystalline hydrocarbon wax or a natural wax, the said wax being at least 30% by weight of the biologically inactive cushioning beads. Such beads are useful for making solid shaped articles containing biologically active ingredients by compression.

26 Claims, 7 Drawing Sheets

LEGEND: ◇ 500 KG
+ 1000 KG
▲ 1500 KG

FIG. 7

LEGEND: ◇ 500 KG

+ 1000 KG

▲ NON-COMPACTED

CUSHIONING WAX BEADS FOR MAKING SOLID SHAPED ARTICLES

The present invention relates to solid, shaped articles, in particular tablets, comprising biologically active substances and to a method for the production of said articles. It also relates to a mixture of an encapsulated biologically active substance and a plurality of cushioning beads comprising a specific wax, the said mixture being suitable for making the solid shaped articles. It further relates to a method of biologically treating a mammal or a plant by using such solid shaped articles.

BACKGROUND OF THE INVENTION

Tablets and capsules are generally unsuitable for administering high doses of biologically active ingredients since individual large dosage forms are difficult to swallow, or necessitate the administration of several tablets or capsules at a time, leading to impaired patient compliance. Chewable tablets are not ideal with young children and older people and are furthermore unsuitable for the incorporation of controlled-release coated pellets which can get crushed upon chewing.

Oral liquid suspensions of pharmaceutical and veterinary ingredients are designed primarily for those who experience difficulty in swallowing solid medication. However, they are not suitable for the incorporation of controlled-release particles into aqueous vehicles, since this often results in premature release of the biologically active ingredient into the suspending media during storage. Various efforts have been made to formulate sustained-release suspensions, the most successful using ion-exchange resins to bind charged molecules. Limitations of this system include low drug-loading capability and its applicability to only ionic drugs.

The formulation of a solid oral dosage form, whether tablet or capsule, which disintegrates rapidly in water to form an instantaneous homogenous suspension of adequate viscosity to be swallowed could circumvent the problems of administering large dosages without premature release from controlled-release particles while providing a ready measured dose. The key to the development of such a dosage form is a rapidly disintegrating tablet which disperses to form a viscous suspension. A delay in the development of a viscous gel is essential for achieving disintegration of the tablet. On the other hand, a rapidly increasing viscosity is necessary to provide adequate suspension properties.

The ideal solid oral dosage form should contain a swellable material which is able to increase viscosity on contact with water, at least one biologically active ingredient for immediate or sustained release delivery of the biologically active ingredient, and a filler conferring compactibility and the capability to disintegrate quickly. The inclusion of a viscosity increasing agent as a fine powder in the tablet matrix without any processing would interfere with disintegration and result in the formation of a voluminous hydrophilic mass which is impossible to disperse. Thus, it is necessary to incorporate such an agent into the tablet as granules or spheres so that the disintegration process occurs before the viscosity increase.

Hard gelatin capsules are well known in the art, especially as a pharmaceutical dosage form. Their sizes have been standard since the start of industrial manufacture their sizes, ranging from 5 (corresponding to a volume of 0.13 ml) up to 000 (volume of 1.36 ml). Thus, when a large amount of ingredient is required for each dosage unit, depending on the bulk density of the formulation, it may be necessary to use large size capsules which are not popular by the patients since thet are too large to swallow or, even worse, a size 000 capsule may be too small to receive the said amount. Beads and coated beads have often been filled into hard gelatin capsules to be used as conventional or controlled release dosage forms, however it is rather difficult to manufacture sustained-release formulations while using a hard gelatin capsule as the dosage form and such attempts have found relatively limited use despite efforts to improve the engineering of such formulations. This is why tablets are generally recognized as the most popular pharmaceutical oral dosage form participating in the comfort of the patient This is especially true of sustained-release tablets which are designed to release the drug slowly after ingestion In this case, patient compliance is improved since the daily number of tablets and the frequency with which the patient has to take these tablets to obtain the desired effect are considerably reduced. With sustained-release tablets, the drug's activity can be extended to take effect throughout the night, so that the patient need not be awakened until morning, thus resulting in time saving for nurses in hospitals.

The concept of tabletting coated biologically active ingredient particles is therefore of interest. Attempts have been made to produce tablets comprising microcapsules because of the known advantages of the latter: the microencapsulated substance is protected from external influences and vice-versa, for example stability is increased, chances of irritations or undesirable reactions with other components in a mixture are reduced or eliminated, unpleasant tastes and smells can be masked. However, compaction of coated beads for making tablets encounters difficult problems. If the beads have been coated by a rate-controlling polymeric cog to sustain biologically active ingredient delivery, cracking of the coating will cause the delivery system to change the rate of biologically active ingredient delivery or immediately release the dose. Preventing cracking of the coating is therefore of utmost importance. Large amounts of carriers have been found necessary m most cases in order to overcome the tendency of microcapsules or coated beads to brittleness by preventing their rupture on compression, thus resulting again in unacceptably large tablets.

The compaction of dry powders consists of two steps: (a) compression of the particulate solid followed by (b) bonding of the particles. The simplest and most frequent means to study the compaction process involves the relationship between punch force and tablet breaking strength i.e. the force required to break a tablet when subjected to a diametral load. Tablet tensile strength measured by diametral compression is also an appropriate parameter since it can be related by a simple equation to the applied lead, the tablet diameter and tablet thickness when a cylindrical tablet fails under tension by splitting cleanly into dimetral halves. One of the effects of powder compaction is an increase in the bulk density of the starting material. Quite often, the relationship between the applied pressure and density or porosity appears linear over the normal tabletting range of the applied pressure.

Compaction of shined release tablets containing coated pellets involves the following critical aspects. When such a dosage form is developed, the coated pellets must withstand the process of compaction without being damaged in order to prevent any undesirable effects on the biologically active ingredient release properties. The type and amount of coating agent, the size of the sub-unit, the selection of external additives having a cushioning effect, and the rate and magnitude of the applied pressure must be carefully considered. The process of bead compaction involves the application of stress to polymer-coated spherical cores. The desirable mechanical properties of coated beads to be compacted into a tablet together with excipients or placebo cushoning beads should be such that they are strong, not brittle and have low elastic resilience. The mechanical properties of both uncoated and coated beads were investigated by Aulton et al, supra who demonstrated that the presence of a film coat applied by means of an aqueous polymeric dispersion of polymethacrylates influenced the crushing strength and the elastic properties of beads: increasing the polymer loading has the effect of increasing the crushing strength of beads, whilst simultaneously enhancing bead resilience (characterized by a reduction in the elastic modulus).

Significant changes were observed between the compaction properties of the powder and pellet forms of the same formulations: the powder formulations deformed plastically and produced stronger compacts, whereas their pellet forms exhibited elastic deformation and brittle fragmentation, which resulted in compacts of lower tensile strength. It was also observed that the biologically active ingredient release rate from spheres coated with acrylate polymers increased with an initial increase in the applied pressure—this being attributed to the cracks in the coat that formed during compaction—but that further increases in pressure a retarded the release profile, possibly due to closer interparticulate contacts within the tablet which partly compensated for the leaks of the pellet coats.

The selection of external additives is also of importance in the design of tablets since these additives are expected to prevent the occurrence of film cracking in the coated subunits. Their compatibility with the biologically active ingredient-loaded pellets, in terms of particle size, is also very critical, since a non-uniform size distribution can cause segregation, resulting in tabletting problems such as weight variation, poor content uniformity, etc. For instance, placebo microspheres with good "compaction" and "cushioning" properties can be used as diluents. Alternatively, small-size biologically active ingredient-loaded pellets improve the content uniformity of low dose biologically active ingredients, however the surface area of pellets to be coated will increase as the size of the pellets deceases.

When using inert "cushioning" beads as diluents, good blending and minimal segregation is essential in order to achieve satisfactory uniformity of weight and content of the tablet dosage form Segregation is influenced by factors such as markedly different particle size, density or shape. In order to minimize the occurrence of segregation between the biologically active ingredient-loaded pellets and the inert diluent cushioning beads, it is deemed necessary to choose inert beads of the same size and approximately the same density as the active pellets. Further, the inert cushioning beads should be mechanically weaker than the coated biologically active ingredient-loaded ones.

Aulton et al, supra, tried to use different approaches to produce inert "cushioning" beads for cushioning of coated biologically active ingredient-loaded sustained action beads in order to prevent segregation due to size or density. Inert beads containing high microcrystalline cellulose levels, by virtue of the inherent bonding capacity of this material, were exceedingly hard. In addition, inert beads containing high lactose levels were also very hard. The replacement of all or part of the granulating water with isopropyl alcohol (in which lactose was insoluble) did not, as expected, enable the preparation of softer inert cushioning beads which would readily Went at low pressure during tabletting: the resulting beads were still too strong and required three times greater applied force than that of the biologically active ingredient-loaded beads before they crush. Thus, it was concluded that the admixture of biologically active ingredient-loaded beads and inert beads was not a viable proposition.

As noted above, conventional highly compactible fillers like microcrystalline cellulose can be mixed with biologically active ingredient-loaded beads and compressed into tablets. It is well known that beads made from microcrystalline cellulose, alone or in combination with brittle materials such as dicalcium phosphate or lactose, are very hard and not easily deformed or broken. However due to particle size differences with active ingredient-loaded beads, segregation occurs and results in weight variation and content uniformity problems. Microcrystalline cellulose granules produced by dry or wet granulation techniques and having similar size as the biologically active ingredient-loaded beads are able to minimize the segregation due to size differences and subsequent problems. However it was noted namely by Millili et al., *Drug Dev.Ind.Pharm.* 16(8):1411–1426 (1990) and by Aulton et al., *Drug Dev.Ind.Pharm.* 20(20):3069–3104 (1994) that such advantage is obtained to the detriment of compactibility. Therefore a need remains for filler beads which, when used in admixture with biologically active ingredient-loaded coated beads and compressed into tablets, will prevent cracking of the coating by keeping a high level of compactibility without giving rise to weight variation and active ingredient content uniformity problems due to segregation during compacting.

Hereinafter will be given a few specific examples of solutions provided in the prior art in order to attempt solving the various above problems. For instance, British patent No. 1,598,458 discloses successful tabletting of microencapsulated pharmacologically active substances having a brittle coating when a fine powder of a polyethylene glycol or another water-soluble natural or synthetic wax having a melting point from 30 to 100° C. is used as carrier in an amount from 2 to 20% by weight calculated on the brittle macrocapsules.

A first approach to produce improved tablets containing biologically active ingredient-loaded particles coated with a coating to sustain the biologically active ingredient action involves the use of flexible plastically deforming polymeric material which will deform under pressure when forming tablets while maintaining the integrity of the coating. For instance, EP-A-355,247 discloses that granules of a pharmaceutical composition, coated with a primary coating layer and optionally with a further protective coating, are compressed and molded together with non-coated components containing at least 10% by weight of non-swelling polymers having a high degree of compressability/moldability and a low degree of desintegration characteristic in order to prevent the destruction of the coating of the coated granules and to control or modulate the desintegration characteristic of the said coating. The non-swelling polymer may be polyvinylacetate, polyvinylchloride, polyethylene or an intestinally soluble polymer such as a cellulose derivative, a styrene-acrylic copolymer or the like. There is no particular limitation or restriction on the compound used as the coating of the coated granules, which among others may be a paraffin, a microcrystalline wax, a higher alcohol, a higher fatty acid or salt thereof, a higher fatty acid ester such as hydrogenated oil, camauba wax, beeswax, and the like. The coating material normally accounts for 1 to 80% by weight of the pharmaceutical composition. According to this document the coated granules may be produced by a conventional granulating method or by microencapsulation and it is also possible to formulate the active ingredient into the non-coated components.

Conventionally in the art, granules are aggregates formed by agglomeration (also referred to as granulation) of powder particles through the sticking together of individual feed material components. Although the said individual components may not segregate, the granules themselves may segregate if there is a wide size distribution. If this occurs in the tablet machines, products having large weight variations will result because these machines fill by volume rather than weight. This will lead to an unacceptable distribution of the biologically active ingredient content within the batch of finished product even though the said ingredient is evenly distributed by weight through the granules. Therefore there is a need for solving the inherent aforesaid disadvantages of granules.

As is well known in the art, beads (or pellets) are distinguishable from granules. Pelletization is an agglomeration process that converts fine powders or granules into small, free-flowing, spherical or semi-spherical units. As opposed to the process of granulation, the production of beads results in a narrow size-range distribution. The more spherical nature of beads compared to granules provides better flow and reduces segregation due to shape differences. Also, the surface morphology of beads is optimal for applying a functional coating.

Hence, a second approach to produce such sustained release tablets involves the mixing and compaction of biologically active ingredient-loaded beads with softer inert cushioning beads which deform at lower pressures during tabletting to prevent the fracture of the coated beads. For instance, WO 97/25029 discloses tablets containing (i) coated pellets of specific diameter and crushability comprising an active ingredient and preferably provided with controlled release properties, (ii) deformable pellets of specific diameter and crushability comprising a plastically deformable material having a melting point of no more man 70° C. such as an ester, ether or salt of a fatty acid having at least 12, preferably around 18 carbon atoms (suitably a glyceryl mono-, di- or triester of palmitic and/or stearic acid), further comprising 10 to 80% of a cellulosic derivative binder and further optionally comprising a water-insoluble inorganic powder diluent and (iii) pellets comprising a disintegrating component, preferably a water-insoluble inorganic salt. The pellets are used in a weight ratio active pellets: deformable pellets:disintegrating pellets in the range 1:(0.2–5.0):(0.2–5.0). In this document, the crushability of the deformable pellets is said to be important to achieve the protection or cushioning of the active pellets in the tabletting procedure. However alternatives solutions within this second approach have often failed. For instance the production of softer inert cushioning beads containing microcrystalline cellulose was not successful when water and/or alcohol was used as the granulating agent.

In order to overturn this difficulty, U.S. Pat. No. 5,780,055 discloses cushioning beads having a diameter of about 0.2 to 2.0 mm, prepared by extrusion-spheronization followed by freeze-drying and comprising microcrystalline cellulose optionally admixed with a disintegrant and/or a filler. The said beads are useful for making tablets when mixed with biologically active ingredient-loaded beads optionally coated with or containing a material for controlled or sustained release properties. The cushioning beads of this document are required to fragment initially into progeny primary powder particles followed by plastic deformation in order to held the tablet together by excipient-excipient contact. This prior art is thus limited to the use of a specific production technology, therefore a need remains for a technical solution to the above disclosed quality problems which can at the same time provide the industrial flexibility associated with the possibility to resort to various production technologies.

In summary, the formulation of ready-made suspensions containing-controlled release beads have been associated with premature leaching of the biologically active ingredient. The use of a dispersible tablet to form an instantaneous suspension can circumvent this problem together with the possibility of administering large doses of biologically active ingredients. The ideal tablet to form an instantaneous sustained release suspension should disintegrate quickly (less than 5 seconds) in water followed by the formation of a viscous suspension (within 1 to 2 minutes) to delay the settling of the biologically active ingredient-loaded membrane-coated beads until the dose is swallowed by the patient. In order to formulate this tablet three components are deemed to be necessary:
(1) biologically active ingredient-loaded membrane-coated beads intended to deliver the dose over a long period of time;
(2) a viscosity enhancer capable of delaying the sedimentation of the biologically active ingredient-loaded beads; and
(3) a filler system capable of producing mechanically strong compacts while protecting the biologically active ingredient-loaded beads from fracturing.

However none of the technical solutions available from the prior art provides the capability of solving the various above-mentioned problems at the same time. The present invention is based on the unexpected observation that the drawbacks of the prior art may be overcome while not requiring that the filler system initially fragment into progeny primary powder particles followed by plastic deformation in order to held the tablet together by excipient-excipient contact. The present invention therefore results from the selection of a cushioning bead meeting this condition

SUMMARY OF THE INVENTION

An object of the present invention is to provide compactible cushioning beads which may be useful for, among others, producing by compaction a wide range of solid shaped articles of biologically active ingredients. Another object of the present invention is to provide water-dispersible tablets having high tensile strength. Still another object of the present invention is to provide tablets containing beads which give rise to sustained delivery of a biologically active ingredient.

Yet another object of the present invention is to provide tablets containing a swellable material able to rapidly generate viscosity when coming in contact with water. An additional object of the present invention is to provide tablets which disintegrate rapidly in water, and form a homogenous suspension which can be easily swallowed by children and the elderly, with minimal effect on the biologically active ingredient release properties. A further object of the present invention is to provide tablets which disintegrate rapidly in water, and form a homogenous suspension when large doses of biologically active ingredient are needed, but where swallowing of a large tablet or capsule raises a problem. Another object of the present invention is to provide tablets which can be manufactured by a wide range of production technologies. Yet another object of the present invention is to provide a method of treatment of a mammal or a plant using ready measured doses of biologically active ingredient even for the administration of large dosages.

These and other objects of the present invention, which will be apparent from the detailed description of the invention provided hereinafter, have been met, in one embodiment, by biologically inactive cushioning beads for making solid shaped articles containing biologically active ingredients by compression, comprising at least one compressible cushioning component consisting essentially of a microcrystalline hydrocarbon wax or a natural wax, the said wax being at least about 30% by weight of the biologically inactive cushioning beads.

DETAILED DESCRIPTION OF THE INVENTION

The present invention may provide biologically inactive cushioning beads comprising at least one compressible cushioning component consisting essentially of a microcrystalline hydrocarbon wax or a natural wax, the said wax being at least about 30% by weight of the biologically inactive cushioning beads and which are useful for making solid shaped articles containing biologically active ingredients by compression.

The present invention may also provide cushioning beads for making solid shaped articles containing biologically active ingredients by compression, comprising at least one compressible cushioning component comprising a hydrocarbon wax or a natal wax, the cushioning beads including at least 5% by weight of an excipient dispersed throughout the hydrocarbon or natural wax. The excipient is preferably a disintegrant.

The present invention may provide a method for treating a plant or a mammal in need of a biological or therapeutic treatment by administering to the mammal or bringing the said plant into contact with an efficient amount of a biologically active ingredient in the form of a solid shaped article containing biologically active ingredient-loaded beads and further comprising biologically inactive cushioning beads comprising at least one compressible cushioning component comprising a hydrocarbon wax or a natural wax, the cushioning beads also including at least 5% excipient dispersed throughout the wax. The excipient is preferably a disintegrant.

The present invention may also provide a method for treating a mammal or a plant in need of a medication by administering to said mammal or contacting the plant with an efficient amount of a biological or therapeutic treatment with a substance containing a biologically active ingredient in the form of a solid shaped article containing biologically active ingredient-loaded beads and further comprising biologically inactive cushioning beads comprising at least one compressible cushioning component consisting essentially of a microcrystalline hydrocarbon wax or a natural wax, the said wax being at least about 30% by weight of the biologically inactive cushioning beads.

The term "microcrystalline hydrocarbon wax" is used herein to mean a refined synthetic wax derived from petroleum, having a dynamic viscosity at 98.9° C. (DIN 52007) greater than or equal to about 2 mPa.s and meeting U.S.Food and Drug Administration (FDA) standards. The said wax may, if needed, be characterized by further parameters like refractive index, melting point (ASTM D3945), congealing point (ASTM D 938 or DIN ISO 2207), penetration (ASTM D 1321 or DIN 51579), odour (ASTM D1833), ultraviolet absorption (21 CFR 172.886) and colour (ASTM D1500). According to the present invention, preference is given to water-insoluble microcrystalline hydrocarbon and natural waxes.

A microcrystalline hydrocarbon wax for use in the present invention may be obtained from the highest boiling fraction of a crude oil, hence its detailed constitution depends on the source of the crude oil and the degree of refining to which it has been subjected prior to wax separation and refining. As is well known in the art, microcrystalline hydrocarbon waxes display physico-chemical properties quite different from paraffin waxes (for instance much higher molecular weights) and have a very delicate crystalline structure, the crystals of which may be of a fine needle or short plate type.

In the manufacture of conventional microcrystalline hydrocarbon waxes, the bottom stream from a vacuum tower or "bright stock" is deasphalted to produce a heavy residual oil which is then extracted to partially remove aromatics. Hydrocarbonaceous feeds from which underwaxed bright stocks may be obtained usually contain aromatic compounds as well as normal and branched paraffins of very high chain lengths. These feeds usually boil in the gas oil range. Typical feedstocks are vacuum gas oils with normal boiling ranges above about 350° C. and below about 600° C., and deasphalted residual oils having normal boiling ranges above about 480° C. and below about 650° C. Reduced topped crude oils, shale oils, liquefied coal, coal, coke distillates, flask or thermally cracked oils and other heavy oils can also be used as the feed source. The "microcrystalline hydrocarbon wax" as used herein may be obtained from a deoiled (i.e. containing less than about 5 weight % oil) wax having a melting point up to about 95° C. which is recovered from this deasphalted, extracted oil by dewaxing and deoiling. The said deoiled wax is characterised by a poor odour and a dark colour and contains aromatic impurities as shown by ultraviolet absorption tests, thus it must be further refined in order to yield a product meeting FDA standards (heavy metal content, ultraviolet absorption, colour, odour, and colour stability). For this purpose, it may be contacted with solid absorbent materials such as bauxite or clay to absorb the aromatic compounds imparting unfavourable properties to the wax. For instance, catalytic refining of the wax in the presence of hydrogen, or hydrofining, is known from U.S. Pat No. 3,052,622 disclosing simultaneously deasphalting and extracting the aromatics via the so-called Duo-Sol process to obtain a waxy petroleum residue which is then hydrofined by passing the wax, in the presence of hydrogen, over a catalyst of nickel oxide on bauxite. The hydrofined product is then dewaxed via a conventional solvent dewaxing process using toluene and methylethylketone. Also U.S. Pat. No. 4,608,151 also discloses a process for making a high molecular weight microcrystalline hydrocarbon wax comprising:

in a first step, hydrodenitrification of a hydrocracked underwaxed bright stock using e.g. a sulphurated nickel-tin or nickel-molybdenum hydrotreating catalyst having a siliceous or alumina matrix, in a second step, hydrofinishing the product resulting from first step using, e.g. an unsulphurated nickel-tin or palladium hydrotreating catalyst having a siliceous or alumina matrix, and in the third step, solvent dewaxing the product resulting from second step while using a conventional solvent such as a mixture of methylethylketone and toluene.

For the performance of the present invention, it is preferable to use a microcrystalline hydrocarbon wax having a congealing point between about 50° C. and 90° C. and which is water-insoluble. The microcrystalline hydrocarbon wax usually comprises a mixture of linear (normal) and branched (iso) hydrocarbons, According to a preferred embodiment of the present invention, the said mixture comprises from about 30 to about 90% by weight of linear hydrocarbons and from about 10 to about 70% by weight of branched hydrocarbons. Also preferably, the microcrystalline hydrocarbon wax will be substantially free from unsaturated hydrocarbons. According to another preferred embodiment of the present invention, over 98% of the molecules of the microcrystalline hydrocarbon wax have a molecular chain length (as determined by high temperature capillary gas chromatography) ranging from 20 to 75, most preferably from 20 to 62, carbon atoms.

According to a preferred embodiment of the present invention, the distribution of molecular chain lengths within the microcrystalline hydrocarbon wax is such that less than 6% of the molecules have less than 25 carbon atoms, 6 to 50% of the molecules have 25 to 29 carbon atoms, 20 to 45% of the molecules have 30 to 34 carbon atoms and 7 to 70% of the molecules have at least 35 carbon atoms. More preferably, the said distribution is such that less than 5% of the molecules have less than 25 carbon atoms, 10 to 25% of the molecules have 25 to 29 carbon atoms, 30 to 45% of the molecules have 30 to 34 carbon atoms and 30 to 45% of the molecules have at least 35 carbon atoms.

As a substitute to the microcrystalline hydrocarbon wax obtained through refining or hydrofinishing of a deoiled petroleum wax as disclosed above, a synthetic petroleum wax of similar characteristics (dynamic viscosity, refractive index, distribution of molecular weights, crystalline structure and the like) may also be used within the scope of the present invention, which is the product of catalytic polymerization of ethylene or copolymerization of ethylene with minor amounts of linear alpha-olefins having from 3 to 12 carbon atoms (e.g. propylene, 1-butene, 1-hexene, 1-octene) or maleic anhydride. According to the present invention, such a synthetic petroleum wax is designed to meet the FDA standards and preferably has a number average molecular weight from about 500 to about 1,200. Here again, preference is given to a water-insoluble wax.

As a substitute to the above disclosed embodiments of microcrystalline hydrocarbon waxes, there may also be used natural waxes, preferably their grades meeting FDA standards, or mixtures of such natural waxes, showing essentially similar physico-chemical characteristics (dynamic viscosity, refractive index, distribution of molecular weights, melting point, congealing point, proportions of linear and branched hydrocarbons, and the like), crystalline structure (as determined by those skilled in the art) and behaviour (cushioning effect) when subjected to compression. Examples of natural waxes include vegetable waxes and insect waxes such as, without limitation:

canauba wax, a yellowish-white sticky exsudation on the leaves, berries and stalks of *Copernicia cerifera*, a palm tree found in South America, and especially Brazil. Having a melting point of 84° C., it is available from Pontes Industria de Cera Ltda (Fortaleza, Brazil). It is believed to consist largely of myricyl cerotate (a 56 carbon atoms ester) and myricyl alcohol (30 carbon atoms), candelilla wax, an exsudate on the leaves and stems of *Euphorbia antisyphilitica*, a plant growing in the Chihuahuan desert of northeastern Mexico and southwestern United States. Having a melting point of 71° C., it is available from Multiceras S.A. (Mexico) under the tradename REAL™. Being opaque to translucent, it is extracted by boiling the leaves with water and sulfuric acid in a tank, then skimming off the crude wax (called cerote) floating on the top of the tank, then cooling the cerote and breaking it into smaller pieces before re-heating and removing impurities by passing the liquid wax through a filter press, palm wax, formed on the trunk of *Ceroxylan andicola* in tropical America, lignite wax, having a melting point of 80° C., obtained by exhausting the distillation products of lignite by means of benzene. It is believed to contain montanic acid (29 carbon atoms) together with ceryl montanate (56 carbon atoms) and myricyl montanate (60 carbon atoms), ozokerite, a waxy mixture of hydrocarbons occuring in association with petroleum with often unpleasant odor, ceresin wax, usually defined as a purified form of ozokerite consisting of a mixture of hydrocarbons, namely iso-hydrocarbons, of average molecular weight somewhat higher than that of paraffin wax, lardaceine, a wax formed on the shell of *Ceroplastens rubens*, an insect living on the tea plant, and containing a substantial amount of ceromelissic acid having a melting point of 94° C., and China wax, secreted by the Chinese ash-tree as a result of sting by *Coccus Ceriferus* and mainly containing ceryl cerotate.

As a substitute to the above embodiments of the present invention may also be us d compounds selected from saturated hydrocarbons having from 25 to 31 carbon atoms, saturated alcohols having from 25 to 31 carbon atoms, saturated monocarboxylic acids having from 25 to 31 carbon atoms, esters obtained from the said alcohols and monocarboxylic acids (thus having from 50 to 62 carbon atoms), including for instance:

neocerylic (neocerotic) alcohol (25 carbon atoms), neocerotic (pentacosanoic) acid (25 carbon atoms), ceryl cerotate (52 carbon atoms), montanic (nonacosanoic) acid (29 carbon atoms), myricic alcohol or hentriacontanol (31 carbon atoms), cerylic (cerotic) alcohol or heptacosanol (27 carbon atoms), cerylic (hexacosanoic) acid (26 carbon atoms), myricyl cerotate (56 carbon atoms).

as well as their mixtures in proportions providing characteristics (dynamic viscosity, refractive index, distribution of molecular weights, melting point, congealing point, proportions of linear and branched hydrocarbons, crystalline structure and the like) similar to those of the synthetic and natural waxes described hereinbefore.

In addition to the microcrystalline hydrocarbon wax or natural wax of substantially Similar characteristics, the cushioning beads of the present invention may include up to about 70% by weight of another compressible biologically inactive cushioning component or at least a biologically inactive but pharmaceutically acceptable additive (excipient) such as colorant, sweetener (e.g. sucrose, mannitol saccharin and aspartame), flavoring agent (e.g. vanillin), buffering agent, filler, disintegrating agent and/or swellable material. Preferably the cushioning beads of the present invention include at least about 5% by weight of at least one such biologically inactive pharmaceutically acceptable additive (excipient) distributed throughout the beads, for instance in the form of an intimate mixture of wax and excipient. A disintegrating agent is especially useful as an excipient for providing quick-disintegrating characteristics when making a solid shaped article containing biologically active ingredients by compression.

Swellable materials (also called viscosity enhancers) are substances which form colloidal dispersions in an aqueous environment, the colloidal particles forming a three-dimensional network or grid-like structure throughout dispersion may become less viscous or dissolve in response to pH changes or enzymes degradation, in such a way that diffusion through the gel does not influence the release of active substance from the particles. The particular swellable material used is not critical to the present invention : examples of useful swelling agents include hydrophilic polymers, such as sugars (dextrose, glucose and sucrose), certain cellulose derivatives such as such as sodium or calcium carboxymethylcellulose, hydroxypropyl cellulose or hydroxypropylmethyl cellulose, pregeletanized starches, polysaccharides, pectin agar, carrageenan, clays, hydrophilic gums like acacia gum, guar gum, arabic gum and xanthan gum, alginic acid, algmates, dextran, pectins (available under the tradenames Visquick® and InstaThick® from Zumbro Inc., Hayfield, Minn.) and carbomer resins.

Carbomer resins (available under the tradenames Carbopol® 934P, 971P and 974P pharmaceutical grades from B.F.Goodrich Cleveland, OH.) are crosslinked acrylic acid polymers wherein a high percentage of carboxylic acid groups allow the resins to be water-swellable. In the presolvated dry state, a carbomer is tightly coiled. When dispersed in water, carbomer begins to hydrate and uncoil, resulting in partial increase of viscosity. It must completely uncoil to achieve the highest and most consistent viscosity, for instance by neutralization by means of a water-soluble base such as ammonia. Neutralization results in ionizing the carbomer and generating negative charges along the polymer backbone. Repulsion of these negative charges causes expansion of the molecule, thereby causing the molecule to rapidly thicken. Overneutralization by strong bases can collapse the resin structure, resulting in a permanent loss of viscosity. Carbomers vary by molecular weight, degree of crosslinking and molecular architecture. These differences are responsible for the specific rheological characteristics and thickening efficiency of each carbomer resin. Neutralized carbomers available under the tradenames Carbopol® EX161 and EX214 from B.F.Goodrich are salts which do not require the addition of a base for use in sustained-release oral suspensions. In solid dosage formulation, Carbopol 934 has also been used as dry tablet binder and as controlled release agent via a hydrophilic matrix mechanism. Carbomer resins not only thicken solutions, but also provide a wide range of flow properties. Like numerous polysaccharide thickeners, such as modified cellulosics and natural gums, carbomer resins are shear thinning (viscosity decreases with increasing shear rate). However, unlike most linear polysaccharides, carbomer resins display plastic rheological profiles. Carbomer solutions will not flow until a minimum force, called the yield value is reached. Carbomer reins provide excellent stability to oil-in-water (otw) emulsions and suspensions. When used in conjunction with appropriate emulsifying agents and coemulsifiers, carbomer resins provide long term stability at ambient and elevated temperatures, as well as under freeze-thaw conditions. The yield value created by carbomer resins prevents "creaming" or separation of o/w emulsions by suspending and separating the oil droplets. It also allows particles to be permanently suspended throughout the medium, creating stable non-settling products, even when used at very low concentrations. One major difficulty encountered with carbomer, is its poor dispersibility: the dry powder resins are highly hygroscopic and hydrate rapidly when added to water or polar solvents. Thus carbomer resins will clump or incompletely hydrate when haphazardly introduced into water because the surfaces of the wet agglomerates quickly solvate and form a layer which prevent rapid wetting of the dry interior. This, together with the fluffy nature of carbomer, results in dispersion defects, such as grainy texture, reduced viscosity or the presence of partially wet agglomerates. Therefore, to avoid lengthy mixing times and to prepare high quality, reproducible carbomer resin dispersions, either proper dispersion techniques should be used or carbomer should be formulated in a readily dispersible less fluffy form, such as granules or spheres, or powder-layered on the surface of carrier seeds. In powder-layering, the biologically active ingredient does not come in contact with the binder solution until it is sprayed onto the inert seed material, as the binder and biologically active ingredient are sprayed from different ports. As the amount of binder solution needed is much less when compared to other layering techniques, drying will be very fast and the total process is much faster.

The particular disintegrating agent which may be used in the cushioning beads is not critical to the present invention. It includes not only water-insoluble inorganic salts such as baryum sulfate, calcium and magnesium carbonates (creating carbon dioxide in situ in effervescent tablets), calcium phosphate, iron oxide, magnesium oxide, dicalcium hydrogenophosphate and their mixtures but also pregelatinized or modified stashes such as sodium starch glycolate (available under the tradenames Primojel® and Explotab®), crosslinked polyvinylpyrrolidone (available under the tradename Polyplasdone XL® from ISP Technologies, Wayne, N.J.), magnesium aluminum silicate (available under the tradename Veegum®), sodium carboxymethylcellulose (available under the tradename Nymcel®) and other cellulose materials (such as available under the tradename Avicel® from FMC Corp., Philadelphia, PA.), cation exchange resins (such as the potassium salt of a crosslinked carboxylic acid resin available under the tradename Amberlite ® IRP), modified cellulose gums such as croscarmellose sodium (available under the tradenames Ac-di-sol® from FMC Corp., Philadelphia, PA.) and the like. The amount of disintegrant used is also not critical to the present invention and depends, in a manner well known in the art, upon the desired granular density (usually in the range of 0.5 to 1.5 mg/ml), porosity and compactibility (usually which upon compaction provides a friability of no more than 1%).

Fillers which may be used in the cushioning beads are not critical to the present invention. They include for instance binding agents such as starch, gelatin, glucose, alginic acid, sodium and calcium alginates, water-soluble acrylic polymer, polyvinylpyrrolidone, ethylcellulose, hydroxypropylmethylcellulose and the like, glidants such as fumed (colloidal) silica (such as available under the tradename Aerosil), lubricants such as magnesium stearate, talc, sodium and magnesium: lauryl sulfates, water-insoluble diluents such as dicalcium phosphate and water-soluble diluents such as lactose, sorbitol and the like.

The cushioning beads of the present invention preferably have an average particle size of about 0.5 to about 2.0 mm and most preferably from 0.75 to 1.25 mm. They can be produced by a number of different techniques such as high-shear mixing, extrusion, extrusion-spheronization or by other means, as long as the said technique results in free-flowing beads, not granules, having a narrow size distribution range. The preferred production process involves high-shear mixing of the microcrystalline hydrocarbon wax or natural wax of similar characteristics and the optional additives (excipients) in view to achieve the average particle size mentioned above. As used herein, the term "high-shear mixing" means mixing the beads components at a high shear rate as is readily known to those skilled in the art. When high-shear mixing is used as the production technique, the temperature of mixing and should preferably be in the range of about 45 to about 60° C., most preferably in the range of about 50 to about 55° C.

Another production process involves fusing the microcrystalline hydrocarbon wax or natural wax of similar characteristics and the optional additives (excipients), for instance by hot stage extrusion, and next feeding the fused mass onto a spheronizer. According to another embodiment of the present invention, extrusion-spheronization may be carried out by a method comprising the steps of:

(a) granulating the microcrystalline hydrocarbon wax or natural wax of similar characteristics and the optional additives in the presence of a granulating fluid, and (b) extruding the granulate obtained in step (a) onto a spheronizer.

Spheronization was first disclosed in U.S. Pat. No. 3,277,520 and equipment design change has been minimal since then. The spheronizer consists basically of a grooved horizontal plate rotating at high speed-within a stationary vertical cylinder fitted with a door to allow release of the pellets. Although extrusion is usually regarded as a continuous process, spherorization equipment design limits the extrusion-spheronization process to a batch process or multiple batch process. The granulating fluid may be water or an aqueous solution containing a lower alcohol, such as ethanol or propanol. The amount of granulating fluid used affects the mechanical properties (porosity, density, friability and compactibility) of the beads produced. The amount of granulating fluid used depends on the composition of the powder mixture used in step (a) and is generally such as to provide a final solids concentration, of about 20 to 80% by weight. The granulating fluid content and composition of the powdery mixture granulated in step (a) must be carefully selected in order that a suitable plastic deformability (extrudability) is obtained. The particle size distribution of the beads obtained is also primarily determined by the extrudate density and granulating fluid content.

In view of their properties, the cushioning beads such as disclosed above are useful for, among others, producing by compaction a wide range of solid shaped articles of biologically or therapeutically active ingredients. Thus a second object of the present invention consists of a solid shaped article containing biologically active ingredient-loaded beads and further comprising biologically inactive cushioning beads comprising at least one compressible cushioning component consisting essentially of a microcrystalline hydrocarbon wax or a natural wax, the said wax being at least about 30% by weight of the biologically inactive cushioning beads.

The term "solid shaped article" as used herein means any article being in a hard solid state at temperatures not exceeding about 60° C. and having a definite geometrical shape, such as for instance ordinary tablets, effervescent tablets, multilayer tablets, sustained-release tablets, pills, lozenges and other compressed dosage forms.

The term "biologically active ingredient" as used herein includes any pharmacologically (as well as veterinary) active substance, for instance any drug, medication, dietary supplement or vitamin which may be administered in the form of solid shaped articles such as defined hereinabove and especially any such active substance for which controlled or sustained release is required or recommended. This enables release of the active substance in the duodenum, ileum or colon rather than the stomach or to ensure that the active substance is released at a controlled rate the stomach to decrease the chance of damage to the gastric mucosa. The term "biologically active ingredient" as used herein also includes other substances such as chemicals having biological activity in nature such as fertilizer, pesticides, herbicides, disinfectants and the like, for which slow release may be advantageous and that are required per se in unit form for adding to a predetermined amount of water, solvent or mixtures of solvents to produce a solution of precisely controlled concentration and efficiency. Examples of the latter substances are trace additives for maintaining the safety of water supplies, nutritional and trace additives for fish ponds, and disinfecting agents for swimming pools. Examples of drugs and medications within the scope of the present invention include, without limitation, microencapsulated potassium chloride, lithium salts, acetylsalicylic acid (aspirin), diclofenac sodium, aceclofenac, indomethacin, nonsteroidal anti-inflammatory drugs, calcium salts, antiosteoporotics, muscle relaxants, abortives, alcohol deterrents, anabolics, analgesics, androgens, anorexics, antiamebics, antiarrhythmics, antiarthritics, antibacterials, anticholinergics, anticoagulants, anticonvulsants, antidepressants, antidiabetics, antidiarrheals, antidiuretics, antiemetics, antihistaminics, antihyperlipoproteinemics, antihypertensives, antihyperthyroids, antihypotensives, antimigraine, antiparkinsonians, antipsychotics, antispasmodics, antithrombotics, antiulceratives, antivirals, anxiolytics, bronchodilators, antitussives, antipyretics, calcium regulators, cardiotonics, choleretics, cholinergics, stimulants of the central nervous system, contraceptives, decongestants, diuretics, emetics, estrogens, glucocorticoids, hematinics, hemostatics, immunomodulators, mucolytics, nootropics, progestogens, respiratory stimulants, cerebral, coronary and peripheral vasodilators, vasoprotectants, vitamins, antibiotics and the like.

The particular pesticide used is not critical to the present invention. Examples of such pesticides include clomazone, sulfentrazone, trifluralin and mixtures thereof. The particular herbicide used is not critical to the present invention. Examples of such herbicides include zeta-cypermephrin, cadusafos and bifenthrin. The particular fertilizer used is not critical to the present invention. Examples of such fertilizers include natural phosphates and synthetic superphosphates.

The solid shaped article of the present invention preferably contains the biologically active ingredient in the form of beads having a diameter substantially similar to the diameter of the cushioning wax-containing beads, i.e. a diameter preferably ranging from about 0.5 to about 2.0 mm and most preferably from 0.8 to 1.2 mm.

The means for preparing the biologically active ingredient-loaded beads is not critical to the present invention. For example, the biologically active ingredient-loaded beads can be prepared by techniques well-known in the art such as extrusion-spheronization, solution/suspension layering, powder layering, balling (a pelletization process in which finely divided particles are converted, upon the addition of appropriate quantities of liquid, to spherical particles by continuous rolling or tumbling action) or fluidized bed roto-granulation, as long as the said technique results in free-flowing beads, not granules, having a narrow size distribution range.

Optionally, a coating material may be applied, preferably by means of the film-coating process, to the biologically active ingredient-loaded beads for controlling or sustaining the release properties of the biologically active ingredient or for taste masking or for imparting resistance to gastric fluid. Film coating of a tablet involves the deposition, usually by spraying, of a thin film of polymer surrounding the tablet core. The coating solution contains a polymer in a suitable liquid solvent and optionally mixed together with other ingredients such as plasticizers, pigments and/or colorants. After spraying, the drying conditions permit to remove substantially all of the solvent The particular coating material used is not critical to the present invention, and depends upon the purpose of the coating material, e.g. desired release profile, ability to stay intact and/or to withstand the mechanical stress of compaction without cracking. However, as is readily understandable from the purpose of the present invention, the solid shaped articles of the invention are most useful when the said coating material is brittle. The term "brittle" is used herein to denote a coating that would crack if the solid shaped article is tableted or formed by compression in the absence of the cushioning beads of the present invention. Examples of coating polymers useful for controlling or sustaining the release properties of the biologically active ingredient and/or taste masking include derivates of cellulose such as methylcellulose, hydroxypropylmethylcellulose and ethylcellulose, such as those marketed under the tradenames Surelease® and Aquacoate®, polyvinylpyrrolidone and aminoalkyl methylacrylate copolymers. Examples of coating polymers useful for imparting resistance to gastric fluid include shellac, cellulose acetate phthalate (Aquateric®), cellulose acetate trimelliate, hydroxypropylmethylcellulose phthalate, polyvinyl acetate phthalate (Coateric®), hydroxypropyl methylcellulose acetate succinate, carboxymethylethylcellulose, styrene/acrylic acid copolymers, methacrylic acid copolymers, maleic anhydride copolymers and the like. Examples of plasticizers which may be mixed together with the coating polymer include, without limitation, polyethyleneglycol, glycerol, phthalate esters, triethylcitrate, etc.

The thickness of the coating layer used is not critical to the present invention. It depends upon the desired release profile of the biologically active ingredient and typically is in the nanometer to micron ranges. Alternatively, the above-listed polymers and optionally plasticizers can be incorporated into a matrix system together with the biologically active ingredient-loaded beads to sustain its action, e.g. during dry powder mixing prior to granulation, or in the granulation solution prior to extrusion-spheronization, or within the other techniques conventionally used to produce pellets or beads. In such a case, the amount of polymers and optionally plasticizers is not critical to the present invention, and depends upon the purpose of the material e.g. the desired release profile of the biologically active ingredient.

The weight ratio of cushioning beads to biologically active ingredient-loaded beads is not critical to the present invention and is preferably between about 30:70 and 70:30, most preferably between about 40:60 and 60:40.

The solid shaped articles of the present invention may also contain a swellable material (also called viscosity enhancer) which may be present either as individual beads or may be a component of the biologically active ingredient loaded-beads, if these beads are intended for immediate delivery of the biologically active ingredient, i.e. where no sustained action or coating polymer is used. In the latter case, the amount of viscosity enhancer is not critical to the present invention. Viscosity enhancer beads may be produced by extrusion-spheronization using a water-alcohol solution as the granulating fluid, or by powder-layering. This avoids the detrimental effects of ionic salts or pH modifiers on the ability of the viscosity enhancer to increase viscosity when hydrated. Also, extrusion-spheronization of the viscosity enhancer using a hydroalcoholic granulating fluid reduces the tackiness thereof. The particular water-alcohol solution used is not critical to the present invention and may include ethanol, propanol or a mixture thereof.

When viscosity enhancer beads are present in the solid shaped articles of the present invention, their weight ratio to cushioning beads and/or biologically active ingredient loaded-beads is not critical to the present invention, and depends upon the desired viscosity required to keep the biologically active ingredient-loaded beads suspended until the suspension is swallowed by the patient. Typically, the viscosity enhancer, either as individual beads or as a component of the biologically active ingredient-loaded beads, should be present in an amount to achieve an apparent viscosity at 20° C. of 30 to 3,000 mPa.s, preferably 500 to 1000 mPa.s.

The solid shaped articles of the present invention may also contain components traditionally used in the formulation of such articles, e.g., favoring agents, lubricants, sweeteners, colorants and/or buffering agents, such as those listed above.

The solid shaped articles of the present invention are manufactured by compression or compaction of biologically active ingredient-loaded beads, optionally coated by means of a polymer, and cushioning beads comprising a microcrystalline hydrocarbon wax or a natural wax of substantially similar characteristics. Such a production technique is well known in the art and usually referred as tablet production or tableting. The ingredients in the form of beads (or pellets) are fed into a die, then compressed between punches, and finally the compacted mass is ejected from the die.

This requires that:
the beads must be sufficiently free-flowing to uniformly flow into the relatively small volume of the die in a very short time,
the beads, when subjected to a force from the punches, cohere to form a compact of adequate strength, and
adhesion of the tablet to the punches and dies must be avoided, otherwise damage to both tablet and press will follow when removing the tablet from the die. This can be suitably achieved by compacting a mixture of biologically active ingredient-loaded beads, cushioning beads according to the present invention, and at least a lubricant. The particular lubricant is not critical to the invention and includes, among others, hydrogenated oils.

Detailed operation of tablet presses include embodiments well known in the art such as wet massing, fluidized bed granulation, spray drying, precompression and direct compression, which are all applicable to the present invention.

Tableting of the beads is effected according to the type and ratio of the cushioning beads, biologically active ingredient-loaded beads, and optionally viscosity enhancer beads and other components present in the solid shaped articles of the present invention, as well as the type of coating material, if any, used for the biologically active ingredient-loaded beads. The compression or compaction pressure used in the production of the solid shaped articles is not critical to the present invention and depends upon the above-mentioned parameters and is usually about 5 to 200 MPa, preferably about 10 to 150 MPa.

The present invention also provides a method of biologically treating a mammal or a plant by using solid shaped articles such as described hereinbefore. In particular, the present invention provides a method for treating a mammal in need of a medication by administering to said mammal an efficient amount of said medication containing a biologically active ingredient in the form of a solid shaped article containing the said active ingredient and further comprising cushioning beads comprising a microcrystalline hydrocarbon wax or a natural wax of substantially similar characteristics. The biologically active ingredient may be, in the case of a human, any pharmaceutically efficient compound such as specified above or, in the case of an animal any veterinary substance.

The present invention further provides a method for treating a plant in need of a biological treatment by bringing the said plant into contact with an efficient amount of a biologically active ingredient in the form of a solid shaped article containing the said active ingredient and further comprising cushioning beads comprising a microcrystalline hydrocarbon wax or a natural wax of substantially similar characteristics. If needed, treatment of the plant according to the present invention may be followed by watering the plant in order to facilitate release of the active ingredient.

As is readily apparent, the solid shaped articles of the present invention provide numerous advantages over the prior art when used for the biological treatment of mammals and plants such as mentioned in the above methods of treatment. They are able to provide a formulation which disintegrates rapidly in water to form an instantaneous homogenous suspension of adequate viscosity to be swallowed without premature release from controlled-release particles while providing a ready measured dose, even for the administration of large dosages. When using a viscosity enhancer, the solid shaped article of the present invention are useful for preparing an immediate release suspension (when no coating polymer is provided on the biologically active ingredient-loaded beads or when no polymer is incorporated into the matrix system of the biologically active ingredient-loaded beads) or a sustained release suspension (when such a polymer is coated onto or incorporated into the biologically active ingredient-loaded beads), and rapid disintegration occurs when the solid shaped article of the present invention is immersed in water or an aqueous solution. Disintegration occurs within a couple of seconds and give rise to the in situ formation of a suspension over a period of less than 1 minute. The in situ suspension is useful for preparing sustained release liquid products namely for young children and elderly patients who cannot swallow tablets or capsules, or for patients who require large doses of biologically active ingredients, where swallowing large dosage forms is difficult The following examples are provided for illustrative purposes only and are in no way intended to limit the scope of the present invention In the examples below, all percentages are weight percentages, unless otherwise indicated.

EXAMPLE 1

Specifications of Microcrystalline Hydrocarbon Wax Suitable for Making Cushioning Beads A refined pharmaceutical grade of microcrystalline hydrocarbon wax meeting the requirements for making cushioning beads is commercially available from Paramelt N.V. (Heerhugowaard, Netherlands). Its main physical characteristics are as follows:

congealing point (DIN ISO 2207): 58–62° C.

penetration (DIN 51579): 10–14 1/10 mm melting point (ASTM D 3945): 59–63° C.

refractive index: 1.422–1.426 dynamic viscosity at 98.9° C. (DIN 52007–2): 3–4.5 mPa.s

Figure 2:
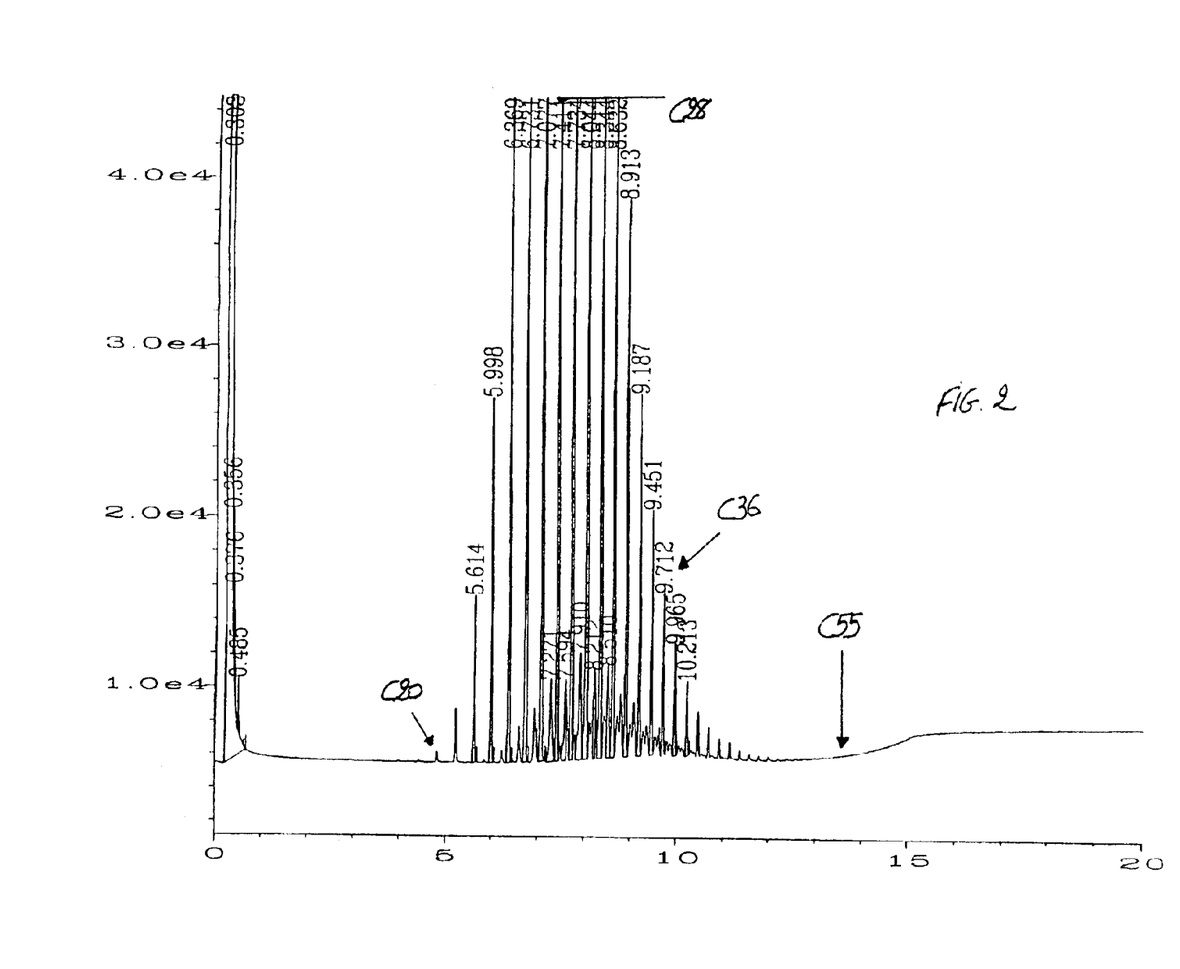
FIG. 2 shows the output of a gas chromatography test for a microcrystalline hydrocarbon wax used in accordance with the present invention.

A representative sample of this microcrystalline hydrocarbon wax was analyzed by gas chromatography, resulting in the chromatograph output given in FIG. 2. This includes a series of well spaced peaks, the distance between two peaks being related to a difference by one atom in the hydrocarbon chain length. The distribution of carbon chain lengths in FIG. 2 shows a nearly symmetrical form around a peak of 28–29 carbon atoms, with a high molecular weight tail above a chain length of 40 carbon atoms. FIG. 2 shows that over 98% of the compounds of this sample have a chain length from 20 to 55 carbon atoms. In more details, the constitution of this microcrystalline hydrocarbon wax according to carbon chain length is as follows:

Chain length group No.1 (from C20 to C24): 5.31%
Chain length group No.2 (from C25 to C29): 48.71%
Chain length group No.3 (from C30 to C34): 38.36%
Chain length group No.4 (from C35 to C39): 6.63%
Chain length group No.5 (from C40 to C44): 0.89%
Chain length group No.6 (from C45 to C49): 0.10%

Figure 1:
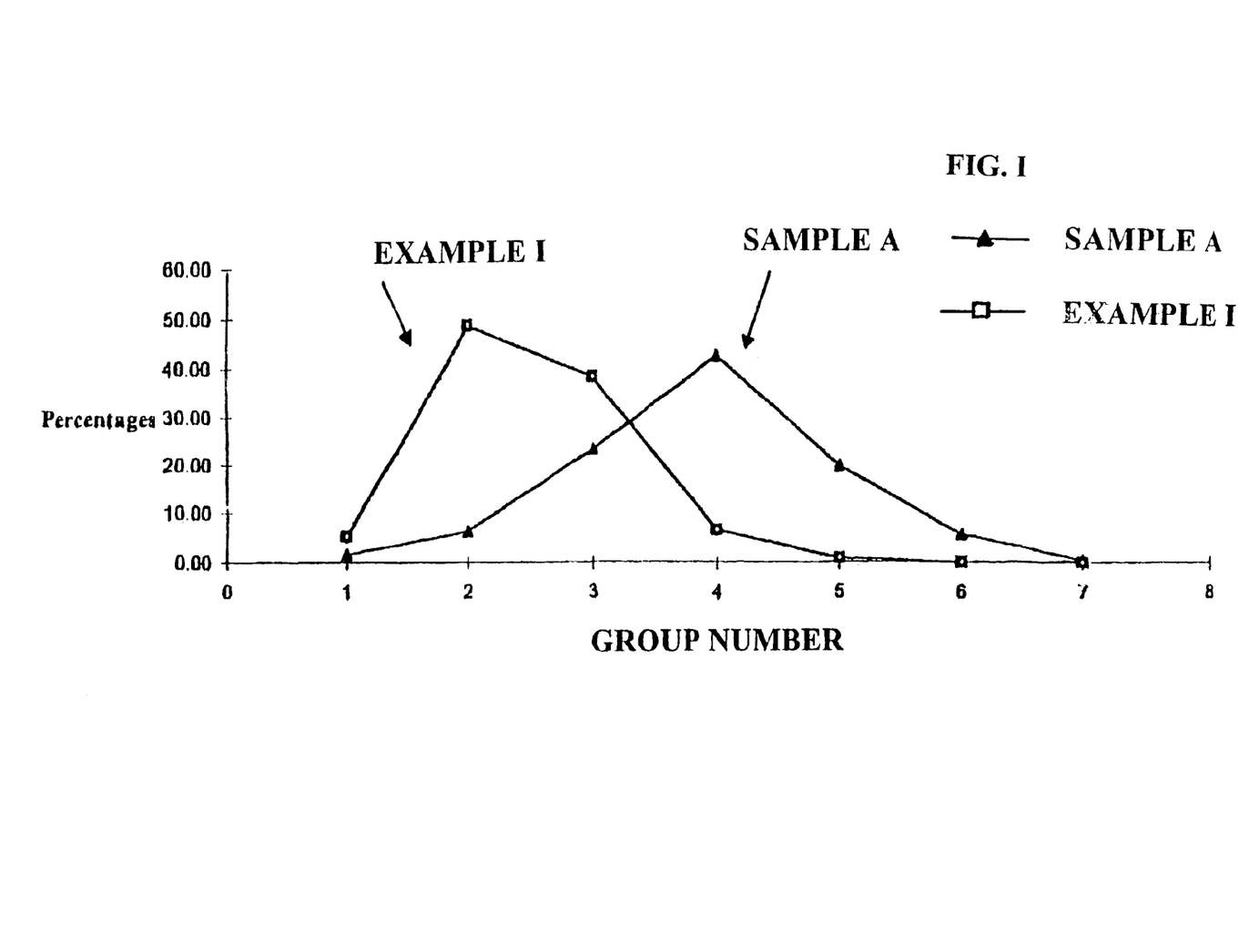
FIG. 1 shows the distribution of molecular chain lengths in various samples of microcrystalline hydrocabon waxes used according to the present invention.

FIG. 1 is a graph representing the above percentages per chain length group for this sample and for sample A (see example 6 hereafter) of another microcrystalline hydrocarbon wax from the same supplier Paramelt N.V.

EXAMPLE 2

Manufacturing of Cushioning Beads Comprising Microcrystalline Hydrocarbon Wax

Blending of a mixture comprising:
Microcrystalline hydrocarbon wax of example 1 12.5 kg
Drum duid corn starch (Cerestar, Vilvoorde, Belgium) 8.35 kg
sodium starch glycolate Explotab® (Barentz, Zaventem, Belgium) as a disintegrating agent: 4.15 kg
is performed in a high shear mixer (Vactron 75, GEI Collette, Wommelgem, Belgium). The different ingredients are mixed in the mixing bowl and next head. The temperate of the jacketed bowl is set at 70° C. and the powder mixture is homogenised during 35 minutes, after which time the mixture is becoming plastic and the temperature of the mixture is 58° C. During heating and homogenisation of the powder, the mixing arm is set at 100 rpm. Next the cooling phase is started by adding 1 kg $CO_2$ pellets and the mixing and chopper arms are set at 200 rpm. Some more $C_2$ pellets are added up to a total amount of 25 kg. After 15 minutes mixing time, the temperate reaches 50.5° C. The energy transfer from the mixing and chopper arms allows a temperature increase up to 52.5° C. and this temperature is kept by adding another 0.5 kg of $C_{O2}$ pellets. After a pelletization period of 7 minutes the bowl is opened and the pellet mass is taken from the bowl and sieved using the appropriate sieves, yielding particle sizes ranging from 0.75 to 125 mm and an average size of 1 mm.

EXAMPLE 3

Production of Tablets Comprising Microcrystalline Hydrocarbon Wax Cushioning Beads Round flat tablets (13 mm) containing diltiazem a calcium channel blocker with coronary vasodilating activity falling in the therapeutic categories of antianginals, antihypertensives and antiarrhythmics, as the biologically active ingredient are produced using the following composition:

Diltiazem coated pellets 57.90%
Cushioning beads of example 2 38.6%
Explotab® 2.5%
Lubritab® 1.0%

The above mixture is first homogeinized during 10 minutes and then compacted by means of an excentric tabletting machine while filling the matrix hole with 800 mg of the said mixture, thus achieving an initial compaction pressure of 500 kg. Thanks to the use of Lubritab®, a hydrogenated oil, as a lubricant in the above formulation, it was possible to prevent adhesion of the resulting tablet to the compacting machine and consequently to avoid damage to the tablet during its ejection from the said machine. Similar tablets may be obtained while using compaction pressures of 1,000 and 1,500 kg respectively.

EXAMPLE 4

Production of Tablets Comprising Microcrystalline Hydrocarbon Was Cushioning Beads Round flat tablets (13 mm) containing diltiazem as the biologically active ingredient are produced by the same process as in example 3 with compaction pressures of 500 kg and 1,000 kg respectively, using the following composition:

Diltiazem coated pellets 58.14%
Cushioning beads of example 2 38.76%
Ac-di-Sol® 2.00%
Lubritab® 1.00%
Aerosil ® (fumed silica) 0.10%

EXAMPLE 5

In vitro Dissolution Profile of Tablets Comprising Microcrystalline Hydrocarbon Wax Cushioning Beads The dissolution profiles of the tablets produced in example 3 were determined while using a dissolution testing apparatus VK 8000 (Vankel Industries Inc., New Jersey) and using the following dissolution parameters:

dissolution medium: distilled water
volume of dissolution medium: 900 ml
rotating speed: 0 rpm
temperature: 37.5° C.
sampling times: 0.5, 1, 2, 4, 8 , 12 and 16 hours
same volume: 5 ml
concentration determination method: spectrophotometry at 240 (Perkin-Elmer, Lamda 12).

Figure 6:
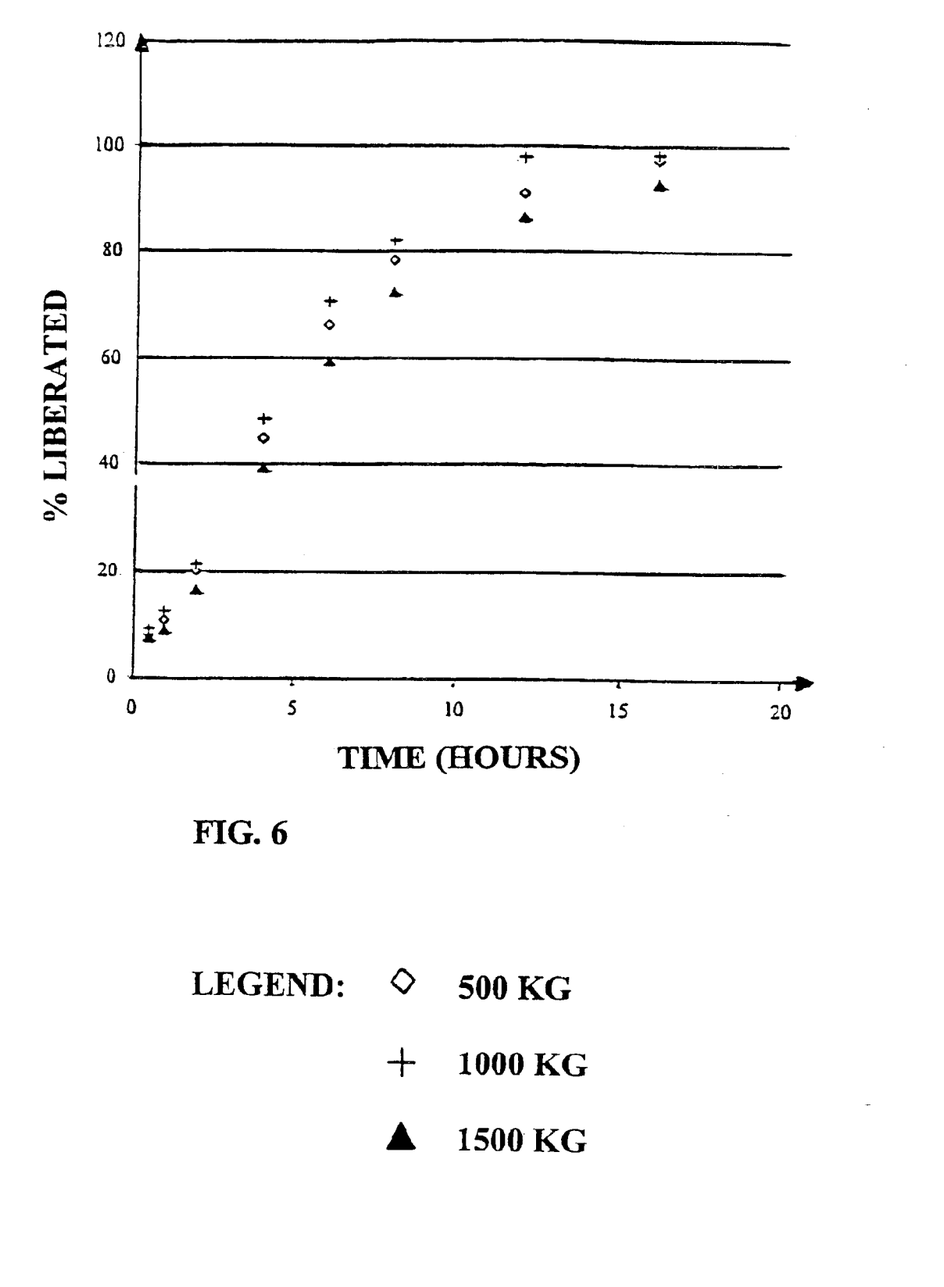
FIG. 6 shows the dissolution profile of a first formulation of tablets comprising beads of a microcrystalline hydrocarbon wax according to the present invention.

The results of such determinations are represented in FIG. 6 showing dissolution percentages as a function of time for tablets compressed at pressures of 500 kg, 1,000 kg and 1,500 kg respectively. These results show that the dissolution profile improves when the compaction pressure increases up to 1,000 kg and then decreases when the compaction pressure further increases up to 1,500 kg. Anyhow, a dissolution percentage of at least 80% is readily achievable within 8 hours when properly selecting the compaction pressure.

EXAMPLE 6

Figure 7:
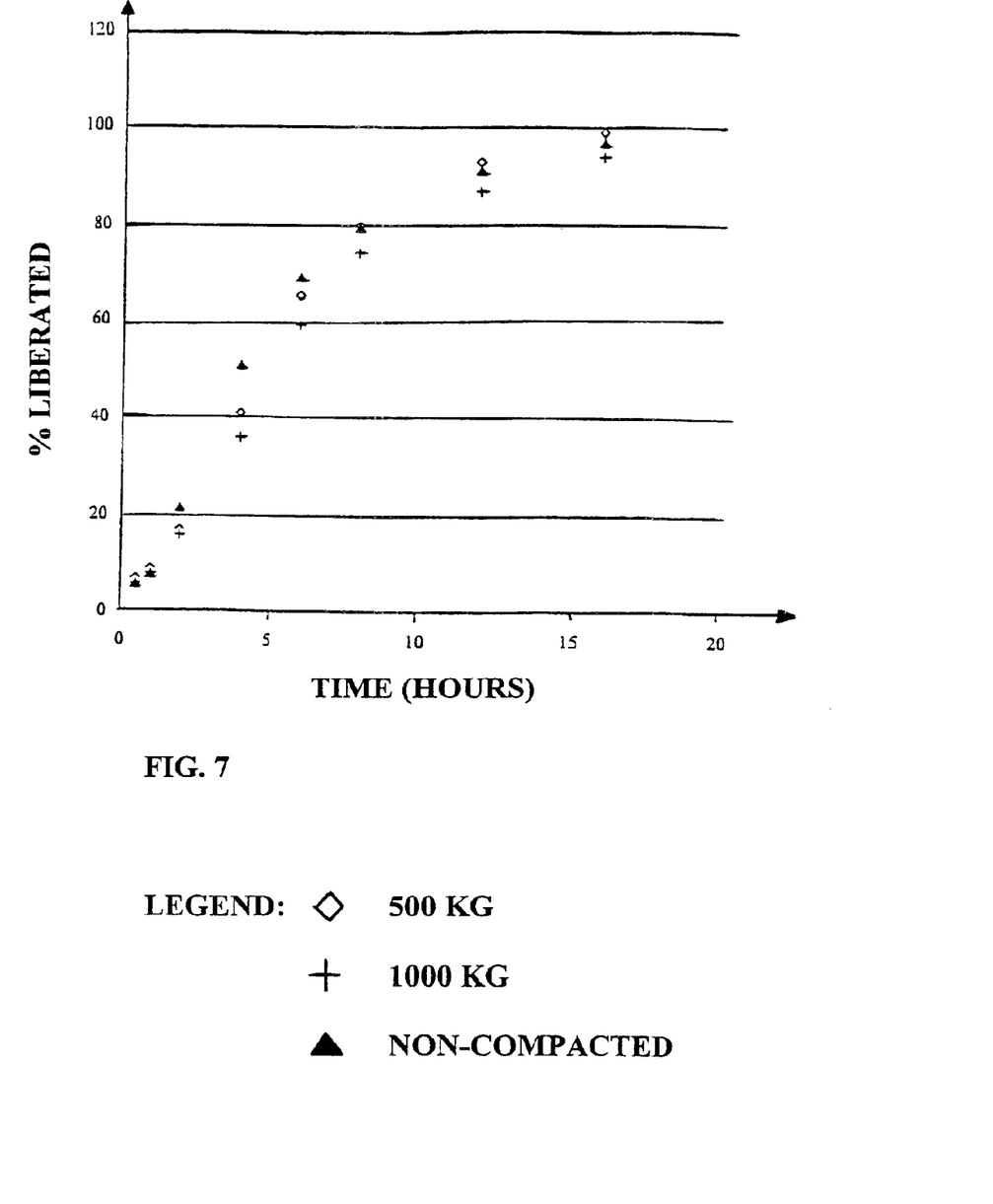
FIG. 7 shows the dissolution profile of a second formulation of tablets comprising beads of a microcrystalline hydrocarbon wax according to the present invention.

In vitro Dissolution Profile of Tablets Comprising Microcrystalline Hydrocarbon Wax Cushioning Beads The dissolution profiles of the tablets produced in example 4 were determined according to the same method as in example 5. The results of such determinations are represented in FIG. 7 showing dissolution percentages as a function of time for tablets compressed at pressures of 500 kg and 1,000 kg respectively. These results show a better dissolution profile for a compaction pressure of 500 kg. Again, a dissolution percentage of 80% is readily achievable within 8 hours by properly selecting the compaction pressure. FIG. 7 also provides the dissolution profile of a non-compacted diltiazem pellets for purpose of comparison.

EXAMPLE 7

Specifications of Other Microcrystalline Hydrocarbon Waxes Suitable For Making Cushioning Beads Other products suitable for making cushioning beads are pharmaceutical grades of microcrystalline hydrocarbon waxes available from Paramelt N.V. (Netherlands), for which gas chromatography analysis of representative samples A and B provides the distribution of hydrocarbon chain lengths as indicated in the table below.

| Carbon chain length range | sample A | sample B |
|---|---|---|
| C20–24 - group 1 | 1.65 | 3.73 |
| C25–29 - group 2 | 6.37 | 16.97 |
| C30–34 - group 3 | 23.36 | 36.85 |
| C35–39 - group 4 | 42.52 | 18.74 |
| C40–44 - group 5 | 19.84 | 7.52 |
| C45–49 - group 6 | 5.82 | 3.92 |
| >= C50 - group 7 | 0.44 | 12.17 |

Figure 3:
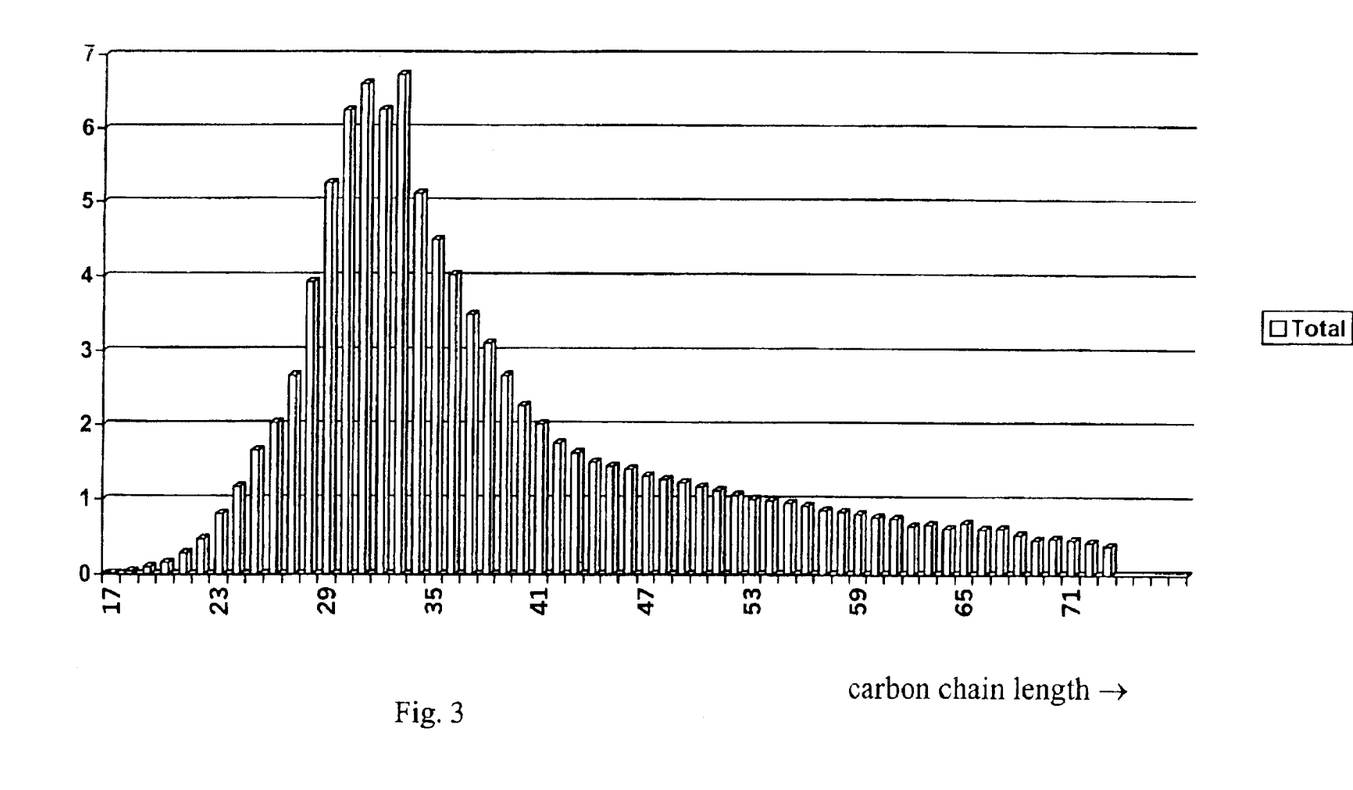
FIG. 3 shows the percentage of hydrocarbons of all kinds as a function of the hydrocarbon chain length in a microcrystalline hydrocarbon wax used according to the present invention.
Figure 4:
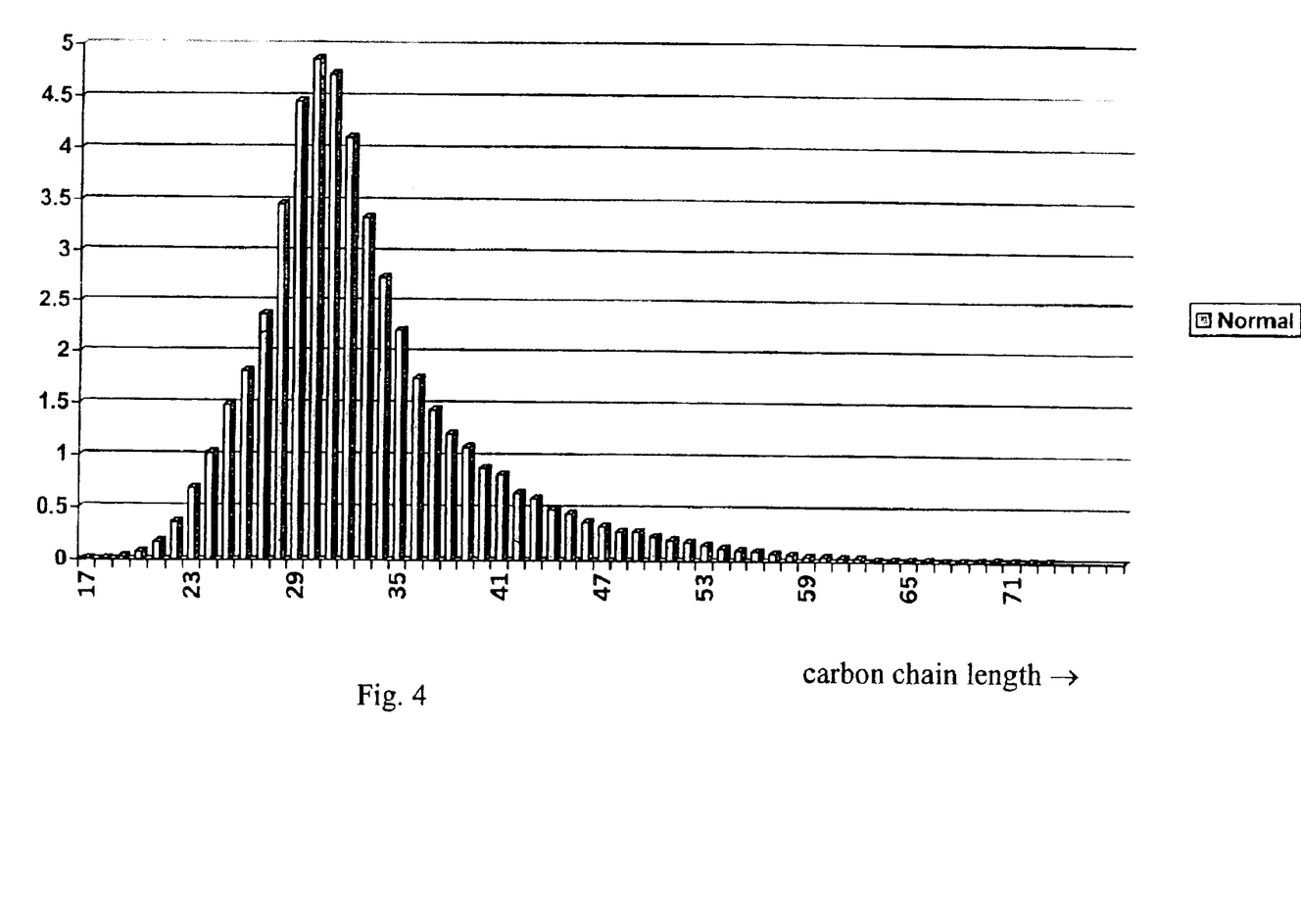
FIG. 4 shows the percentage of linear (normal) hydrocarbons as a function of the hydrocarbon chain length in a microcrystalline hydrocarbon wax used according to the present invention.

A more detailed analysis of sample B has been made using high temperature capillary gas chromatography in order to discriminate and quantify the normal (linear) forms from the branched (iso-) forms of the homologous series of hydrocarbons which make up this microcrystalline wax. The percentages of hydrocarbon as a function of the hydrocarbon chain length are shown in FIGS. 3 to 5 where:

FIG. 3 relates to hydrocarbons of all kinds (linear and branched),

FIG. 4 relates to linear (normal) hydrocarbons, and

Figure 5:
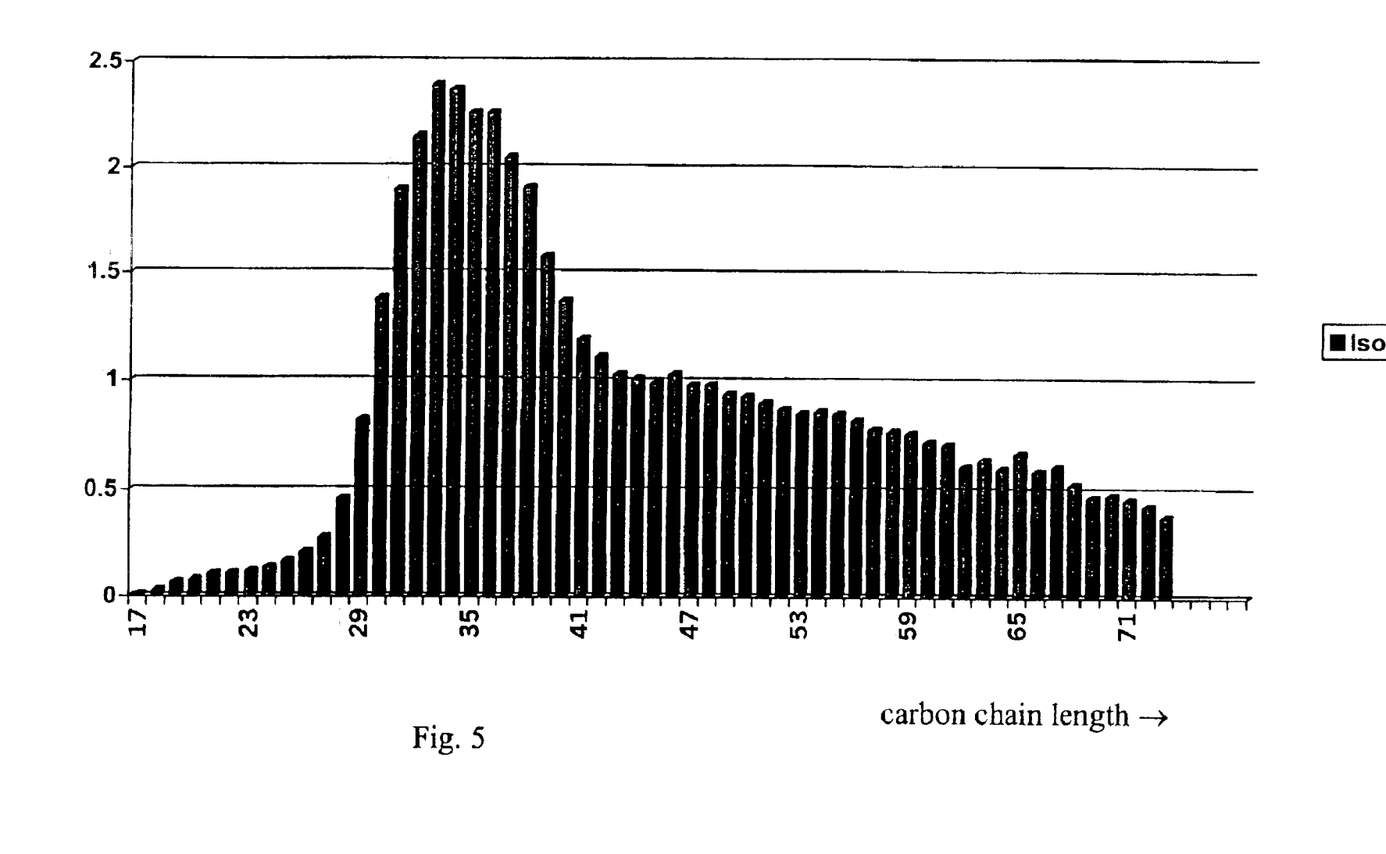
FIG. 5 shows the percentage of branched (iso) hydrocarbons as a function of the hydrocarbon chain length in a microcrystalline hydrocarbon wax used according to the present invention.

FIG. 5 relates to branched (iso) hydrocarbons.

It is remarkable that the distribution of iso-hydrocarbons shows a peak (most common chain length) at 34 carbon atoms which is significantly higher than the peak for the distribution of linear hydrocarbons (30 carbon atoms). The average number of carbon atoms is 29 for the distribution of linear hydrocarbons, 39 for the distribution of iso-hydrocarbons and 33 for the distribution of all hydrocarbons. Calculations from FIGS. 3 to 5 indicate that the normal to iso-hydrocarbon ratio is about 60 to 40 in this sample.

What is claimed is:

1. In a solid shaped compressed article, said solid shaped compressed article containing a biologically active ingredient and a hydrocarbon wax or natural wax, the improvement wherein:

said solid shaped compressed article contains the biologically active ingredient in the form of biologically active ingredient-loaded beads with a brittle coating, said solid shaped article further comprises biologically inactive cushioning beads of a size of about 0.5 to 2 mm for protecting said brittle coating during compression or compaction, wherein said biologically inactive cushioning beads comprise at least one compressible cushioning component consisting essentially of a microcrystalline hydrocarbon wax or a natural wax, the said wax being at least 30% by weight of the biologically inactive cushioning beads, and optionally up to 70% by weight of another biologically inactive compressible cushioning component or pharmaceutically acceptable excipient, and wherein the weight ratio of the biologically inactive cushioning beads to the coated biologically active ingredient-loaded beads is between 30:70 and 70:30.

2. A solid shaped article according to claim 1, wherein the biologically active ingredient-loaded beads are coated with a coating material for controlling or sustaining the release properties of the biologically active ingredient or for taste masking or for imparting resistance to gastric fluid.

3. A solid shaped article according to claim 1, wherein the cushioning beads include at least 5% by weight of at least a biologically inactive pharmaceutically acceptable excipient.

4. A solid shaped article according to claim 1, wherein over 98% of the molecules of the microcrystalline hydrocarbon wax or natural wax have a molecular chain length ranging from 20 to 75 carbon atoms.

5. A method for treating a plant in need of a biological treatment or a mammal in need of a medication by bringing the said plant into contact with an efficient amount of a biologically active ingredient or by administering to said mammal an efficient amount of said medication containing a biologically active ingredient, wherein the said biologically active ingredient is in the form of a compressed solid shaped article containing biologically active ingredient-loaded beads coated with a brittle coating, and further comprising biologically inactive cushioning beads of a size of about 0.5 to 2 mm protecting said brittle coating during compression, wherein said biologically inactive cushioning beads comprise at least one compressible cushioning component consisting essentially of a microcrystalline hydrocarbon wax or a natural wax, the said wax being at least 30% by weight of the biologically inactive cushioning beads, and optionally up to 70% by weight of another biologically inactive compressible cushioning component or pharmaceutically acceptable excipient, and wherein the weight ratio of the biologically inactive cushioning beads to the coated biologically active ingredient-loaded beads is between 30:70 and 70:30.

6. A method according to claim 5, wherein the cushioning beads include at least 5% by weight of at least a biologically inactive pharmaceutically acceptable excipient.

7. A solid shaped article according to claim 1, wherein the microcrystalline hydrocarbon wax or natural wax has a dynamic viscosity at 98.9° C. (DIN 52007) greater than or equal to 2 mPa.s and/or a congealing point between 50° C. and 90° C.

8. A solid shaped article according to claim 1, wherein the microcrystalline hydrocarbon wax or natural wax comprises a mixture of 30 to 90% by weight of linear hydrocarbons and 10 to 70% by weight of branched hydrocarbons.

9. A solid shaped article according to claim 1, wherein the distribution of molecular chain lengths within the microcrystalline hydrocarbon wax or natural wax is such that less than 6% of the molecules have less than 25 carbon atoms, 6 to 50% of the molecules have 25 to 29 carbon atoms, 20 to 45% of the molecules have 30 to 34 carbon atoms and 7 to 70% of the molecules have at least 35 carbon atoms.

10. A solid shaped article according to claim 1, wherein the microcrystalline hydrocarbon wax is a product of catalytic polymerization of ethylene or copolymerization of ethylene with minor amounts of linear alpha-olefins having from 3 to 12 carbon atoms or maleic anhydride.

11. A solid shaped article according to claim 1, wherein the natural wax is selected from carnauba wax, candelilla wax, palm wax, lignite wax, ozokerite, lardaceine, ceresine wax and China wax.

12. A solid shaped article according to claim 1, wherein the wax comprises compounds selected from saturated hydrocarbons having from 25 to 31 carbon atoms, saturated alcohols having from 25 to 31 carbon atoms, saturated monocarboxylic acids having from 25 to 31 carbon atoms, esters obtained from the said alcohols and monocarboxylic acids and having from 50 to 62 carbon atoms, and their mixtures.

13. A solid shaped article according to claim 1, wherein the cushioning beads have an average particle size of 0.5 to 2.0 mm.

14. A method according to claim 5, wherein the microcrystalline hydrocarbon wax or natural wax has a dynamic viscosity at 98.9° C. (DIN 52007) greater than or equal to 2 mPa.s and/or a congealing point between 50° C. and 90° C.

15. A method according to claim 5, wherein the microcrystalline hydrocarbon wax or natural wax comprises a mixture of 30 to 90% by weight of linear hydrocarbons and 10 to 70% by weight of branched hydrocarbons.

16. A method according to claim 5, wherein the distribution of molecular chain lengths within the microcrystalline hydrocarbon wax or natural wax is such that less than 6% of the molecules have less than 25 carbon atoms, 6 to 50% of the molecules have 25 to 29 carbon atoms, 20 to 45% of the molecules have 30 to 34 carbon atoms and 7 to 70% of the molecules have at least 35 carbon atoms.

17. A method according to claim 5, wherein the microcrystalline hydrocarbon wax is a product of catalytic polymerization of ethylene or copolymerization of ethylene with minor amounts of linear alpha-olefins having from 3 to 12 carbon atoms or maleic anhydride.

18. A method according to claim 5, wherein the natural wax is selected from carnauba wax, candelilla wax, palm wax, lignite wax, ozokerite, lardaceine, ceresine wax and China wax.

19. A method according to claim 5, wherein the wax comprises compounds selected from saturated hydrocarbons having from 25 to 31 carbon atoms, saturated alcohols having from 25 to 31 carbon atoms, saturated monocarboxylic acids having from 25 to 31 carbon atoms, esters obtained from the said alcohols and monocarboxylic acids and having from 50 to 62 carbon atoms, and their mixtures.

20. A method according to claim 1, wherein over 98% of the molecules of the microcrystalline hydrocarbon wax or natural wax have a molecular chain length ranging from 20 to 75 carbon atoms.

21. In an article containing a biologically active ingredient and a hydrocarbon wax or natural wax, the improvement wherein:
  said article contains the biologically active ingredient in the form of biologically active ingredient-loaded beads of a size of about 0.5 to 2 mm with a brittle coating,
  said article further comprises biologically inactive cushioning beads of a size of about 0.5 to 2 mm with at least one compressible cushioning component comprising a microcrystalline hydrocarbon wax or a natural wax, the said wax being at least 30% by weight of the biologically inactive cushioning beads, and up to 70% by weight of another biologically inactive compressible cushioning component or pharmaceutically acceptable excipient, and
  wherein the weight ratio of the biologically inactive cushioning beads to the coated biologically active ingredient-loaded beads is between 30:70 and 70:30.

22. A method for treating a plant in need of a biological treatment or a mammal in need of a medication by bringing the said plant into contact with an efficient amount of a biologically active ingredient or by administering to said mammal an efficient amount of said medication containing a biologically active ingredient, including
  providing the biologically active ingredient in the form of biologically active ingredient-loaded beads of a size of about 0.5 to 2 mm with a brittle coating,
  providing biologically inactive cushioning beads of a size of about 0.5 to 2 mm with at least one compressible cushioning component comprising a microcrystalline hydrocarbon wax or a natural wax, the said wax being at least 30% by weight of the biologically inactive cushioning beads, and up to 70% by weight of another biologically inactive compressible cushioning component or pharmaceutically acceptable excipient, and 70:30,
  compressing beads wherein the weight ratio of the biologically inactive cushioning beads to the coated biologically active ingredient-loaded beads is between 30:70 and 70:30 to form a solid shaped compressed article, and
  bringing the solid shaped compressed article into contact with said plant or mammal.

23. A solid shaped article according to claim 1, wherein the biologically active ingredient-loaded beads are formed by extrusion-spheronization.

24. A shaped article according to claim 5, wherein the biologically active ingredient-loaded beads are made by extrusion-spheronization.

25. A solid shaped article according to claim 21, wherein the biologically active ingredient-loaded beads are formed by extrusion-spheronization.

26. A solid shaped article according to claim 22, wherein the biologically active ingredient-loaded beads are made by extrusion-spheronization.

* * * * *